United States Patent [19]

Bigge et al.

[11] Patent Number: 5,175,153
[45] Date of Patent: Dec. 29, 1992

[54] SUBSTITUTED ALPHA-AMINO ACIDS HAVING PHARMACEUTICAL ACTIVITY

[75] Inventors: Christopher F. Bigge, Ann Arbor; James T. Drummond, Ypsilanti; Vlad E. Gregor, Ann Arbor; Graham Johnson, Ann Arbor; Michael R. Pavia, Ann Arbor, all of Mich.

[73] Assignee: Warner-Lambert Company, Morris Plains, N.J.

[21] Appl. No.: 256,221

[22] Filed: Oct. 14, 1988

Related U.S. Application Data

[63] Continuation-in-part of Ser. No. 126,372, Nov. 30, 1987, abandoned.

[51] Int. Cl.⁵ .................. C07F 9/38; C07F 9/40; A61K 31/13; A61K 31/185
[52] U.S. Cl. ........................ 514/114; 514/89; 514/119; 546/22; 558/190; 560/16; 560/38; 560/40; 562/10; 562/11; 562/15
[58] Field of Search ............ 260/502.5 D; 558/190; 564/182; 514/114, 89, 119; 560/38, 16, 40; 562/10, 11, 15; 546/22

[56] References Cited

U.S. PATENT DOCUMENTS

| 4,657,899 | 4/1987 | Rzeszotarski et al. | 260/502.50 |
| 4,746,653 | 5/1988 | Hutchison et al. | 514/89 |
| 4,918,064 | 4/1990 | Cordi et al. | 562/11 |

FOREIGN PATENT DOCUMENTS

| 0159889 | 10/1985 | European Pat. Off. . |
| 0203891 | 3/1986 | European Pat. Off. . |
| 87810080.9 | 2/1987 | European Pat. Off. . |
| 0313002 | 4/1989 | European Pat. Off. . |
| 2104078 | 3/1983 | United Kingdom . |
| 2156818 | 10/1985 | United Kingdom . |
| 2198134A | 10/1987 | United Kingdom . |

OTHER PUBLICATIONS

EPO Search Report (EP88 11 99 11) with references.
Neurology and Neurobiology vol. 24, "Excitatory Amino Acid Transmission", 1987 pp. 19–26.
"The Synthesis of p-Substituted D,L-Phenylglycines by the Amidoalkylation of Benzylchloride and N-Benzylbenzamide".
D. Ben-Ishai et al. Tetrahedran, vol. 33, pp. 2715–2717 (1977) SCRIP #1067, Jan. 13, 1986, p. 22.

Primary Examiner—Joseph E. Evans
Attorney, Agent, or Firm—Ronald A. Daignault

[57] ABSTRACT

The present invention is novel substituted α-amino acids, pharmaceutical compositions, method of use, and preparations therefore having utility for treating disorders which benefit from blockade of aspartate and glutamate receptors.

14 Claims, No Drawings

SUBSTITUTED ALPHA-AMINO ACIDS HAVING PHARMACEUTICAL ACTIVITY

This is a continuation-in-part of U.S. Application Ser. No. 126,372 filed Nov. 30, 1987, now abandoned.

BACKGROUND OF THE INVENTION

Among excitatory amino acid receptor antagonists recognized for usefulness in the treatment of disorders are those that block N-methyl-D-aspartate (NMDA) receptors.

For example, heterocycles containing nitrogen, and having phosphonic acid and carboxylate substituents, are found in European Application Publication Nos. 0159889 and 0203891 which disclose utility for the treatment of nervous system disorders. The disorders disclosed which are responsive to blockade of the NMDA receptor include cerebral ischaemia, muscular spasms (spasticity), convulsive disorders (epilepsy), and anxiety. These compounds, however, are readily distinguished from the compounds of the present invention both by the nitrogen containing heterocycles and by the various substituents thereon.

Aliphatic α-amino acids are disclosed in British Patent Nos. 2,104,078 and 2,156,818. The first of these, No. 2,104,078, includes 2-amino-7-phosphonoheptanoic acid (APH) disclosed for use in treating Huntington's disease, Alzheimer's disease, and certain forms of epilepsy as well as for use in the prevention of brain damage associated with stroke (see SCRIP #1067, Jan. 13, 1986, page 22). The second of these, 2,156,818, discloses usefulness for treating epilepsy, disorders associated with excess growth hormone (GH) or luteinizing hormone (LH) secretion, schizophrenia, depression, CNS degenerative disorders, and cerebral hypoxic conditions.

More particularly, U.S. Pat. No. 4,657,899 discloses compounds of the formula

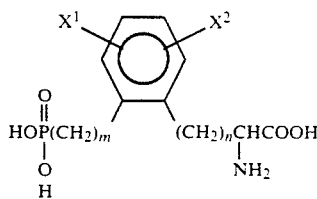

wherein n and m=0, 1, 2, or 3 and $X^1$ and $X^2$ are the same or different and are selected from the group consisting of hydrogen, lower alkyl, halogen, —CH=CH—CH=CH—, amino, nitro, trifluoromethyl, or cyano, having activity as anticovulsants, analgesics, and cognition enhancers through the antagonism of specific excitatory amino acid neurotransmitter receptors.

The novel substituted α-amino acids of the present invention are not made obvious by these disclosures. In fact, clearly the disclosure of U.S. Pat. No. 4,657,899 is limited to a specific ortho positioning of phosphonic acid and amino acid residues on a phenyl ring. Such a limitation teaches away from the novel compounds of the present invention.

An understanding of the role of excitatory amino acids is expanded by J. C. Walkins, et al. in "Recent Advances in the Pharmacology of Excitatory Amino Acids" pp. 19-26 in *Excitatory Amino Acid Transmission: Neurology and Neurobiology*, Volume 24, Ed. by Hicks, Lodge and McLennan, Publisheer: Alan R. Liss, Inc., New York, 1987.

An additional reference is now found to compounds, for example, for the treatment of diseases responding to a blockade of NMDA-sensitive receptors, in European Application Publication No. 0233154, of the formula

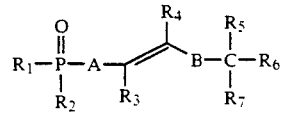

showing a basic difference in that the phosphorus containing substituent and the amino/carboxy containing substituent are linked through a straight chain double bonded C=C linkage and not as substituents on a common aryl ring.

Then, on the other hand antagonists to the NMDA sensitive excitatory amino acid receptors are shown in U.S. Pat. No. 4,746,653, filed Feb. 28, 1986 to include substituted saturated pyridinyl ring systems common to both a phosphorus containing and carboxy or carboxy derivatized substituent.

More recently, the British Patent Application No. 2,198,134 filed Oct. 30, 1986 but not published before Jun. 8, 1988 teaches compounds useful for treating epilepsy including anticonvulsant activity shown from inhibition of NMDA in excitatory amino acid systems having the formula

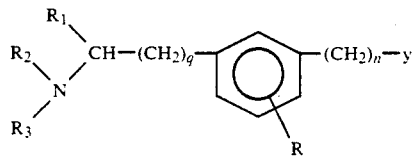

wherein $R_1$ is a carboxy or carboxy containing analogue and y is a

containing substituent. However, the present invention is defined by a scope not taught within the broad disclosure of this application and, therefore, represents an advance not made obvious therein.

Although a related reference teaches "The Synthesis of p-Substituted D,L-Phenylglycines by the Amidoalkylation of Benzylchloride and N-Benzylbenzamide, *Tetrahedron*, Vol. 33, pp. 2715-7 (1977) by D. Ben-Ishai et al, it does not make obvious the use of the process for phosphonate containing derivatives.

SUMMARY OF THE INVENTION

The present invention is a novel compound of the formula I

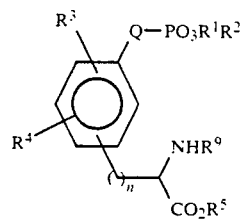

or a pharmaceutically acceptable acid addition, or base salt thereof wherein the group ($I_a$)

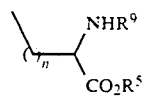

is meta or para to the group ($I_b$)

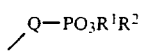

wherein
(1) $n_1$ is 0, 1, or 2;
(2) $R^1$, $R^2$, and $R^5$ are independently hydrogen or a pharmaceutically acceptable labile ester or amide residue;
(3) $R^3$ and $R^4$ are independently hydrogen, hydroxy, lower alkyl optionally substituted by hydroxy or methoxy, aryl, aralkyl, lower alkoxy, $R^{10}S(O)_{0-1}(CH_2)_n$ wherein n is independently as defined above and $R^{10}$ is lower alkyl, halogen, trifluoromethyl, or taken together with adjacent ring carbons are —CH=CH—CH=CH—;
(4) $R^9$ is hydrogen or a protecting group;
(5) Q is —$(CH_2)_m$—, —(CH=CH)—, —$CH_2$—(CH=CH)—, or (CH=CH)—$CH_2$—wherein m is 0, 1, 2, or 3;

with the proviso that when the group $I_a$ is para to the group $I_b$ then n may be 0 when m is 0, 1, 2, or 3 and n may be 1 when m is 0 or 2 and that when the group $I_a$ is meta to the group $I_b$ then n may be 0 when m is 1 or 2, n may be 1 when m is 0, 1, or 2, and n may be 2 when m is 0.

The present invention is also a pharmaceutical composition for the treatment of cerebrovascular disorders in which excitatory amino acid antagonists are useful comprising an amount effective to block glutamate or aspartate (NMDA) receptors of a compound of the formula I as defined above and a pharmaceutically acceptable carrier.

Such disorders include cerebral ischemia or cerebral infarction, resulting from a range of conditions, such as thromboembolic or hemorrhagic stroke, cerebral vasospasm, hypoglycemia, cardiac arrest, and status epilepticus, and also include schizophrenia, epilepsy, neurodegenerative disorders, Alzheimer's disease, or Huntington's disease. Further, cerebrovascular damage may be treated prophylactically or therapeutically where a finite risk of the damage is understood to be present by an ordinarily practicing physician, such as in surgical procedures.

Thus, further the present invention is a method of treating cerebrovascular disorders particularly in which amino acid antagonists are useful in a human suffering therefrom or at risk of such disorders which comprises administering a compound of the formula I as defined above in a unit dosage form.

Finally, the present invention is also novel processes. One of the novel processes is for the preparation of a compound of formula I wherein n is 0 and m is 1, 2, or 3 as defined above which comprises Step (1) reacting a compound of the formula (X)

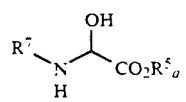

wherein $R_a^5$ is hydrogen and $R^7$ is an acid stable protective group, such as a benzoyl, benzyloxycarbonyl, or ethoxycarbonyl;

with a compound of the formula XI

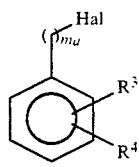

wherein $m_a$ is 1, 2, or 3, Hal is chloro or bromo, and $R^3$ and are as defined above;

in the presence of methanesulfonic acid or strongly dehydrating acids such as concentrated sulfuric acid over a period of forty-eight hours at room temperature to obtain a compound of the formula $XII_a$ when $R^3$ and $R^4$ are H wherein the formula $XII_a$ is

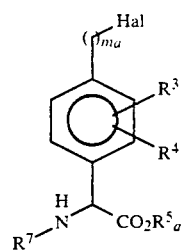

or to obtain a compound of $XII_b$ or $XII_c$ when one of $R^3$ and $R^4$ are not H such that $R^3$ and $R^4$ is selected from a group directing meta or para addition as is known to one of skill in the art;

wherein the formula $XII_b$ is

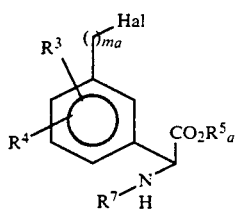

and the formula $XII_c$ is

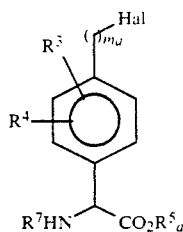

Step (2) the compounds of the formula $XII_a$ are then treated with a compound of the formula XIII

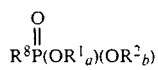

wherein $R^8$ is sodium, potassium, or the like and $R_a{}^1$ and $R_b{}^2$ are lower alkyl;

in a solvent such as tetrahydrofuran, diethyl ether, dimethylformamide, acetonitrile, or the like at temperatures from room temperature to reflux over a period of one to forty-eight hours to obtain the compound of the formula ($XIV_a$). (Alternatively the phosphonoalkyl derivatives of formula $XIV_a$ can be obtained by an Arbuzov reaction with trisubstituted phosphite or an equivalent.)

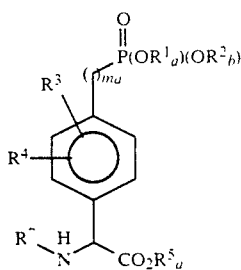

wherein $R^3$ and $R^4$ are hydrogen; or

Step (2) the compounds of the formula $XII_b$ and $XII_c$ are then treated with a compound of the formula XIII

wherein $R^8$ is sodium, potassium, or the like and $R_a{}^1$ and $R_b{}^2$ are as defined above;

in a solvent such as tetrahydrofuran, diethyl ether, dimethylformamide, acetonitrile, or the like at temperatures from room temperature to reflux over a period of one to forty-eight hours to obtain the compound of the formula $XIV_b$ or $XIV_c$. (Alternatively the phosphonomethyl derivatives of formula $XIV_b$ can be obtained by an Arbuzov reaction with trisubstituted phosphite or an equivalent.)

wherein $XIV_b$ is

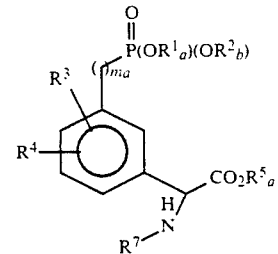

and $XIV_c$ is

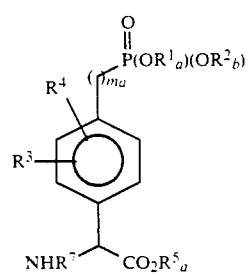

wherein one of $R^3$ and $R^4$ are not hydrogen and $R_a{}^1$, $R_b{}^2$, $R_a{}^5$, $R^7$, and $m_a$ are as defined above; and Step (3) the compounds of the formula $XIV_a$, $XIV_b$, or $XIV_c$ optionally are treated to remove the protective group and treated to acidify the phosphonate residue and optionally treated further to obtain the compounds of formula I wherein n is 0 and m is 0, 1, 2, or 3.

This process is summarized in Scheme A as follows:

Scheme A

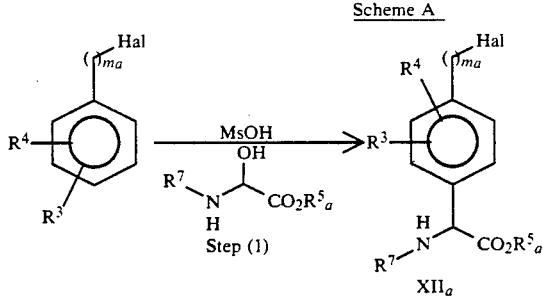

wherein $R^3$ and $R^4$ are hydrogen or

Scheme A -continued

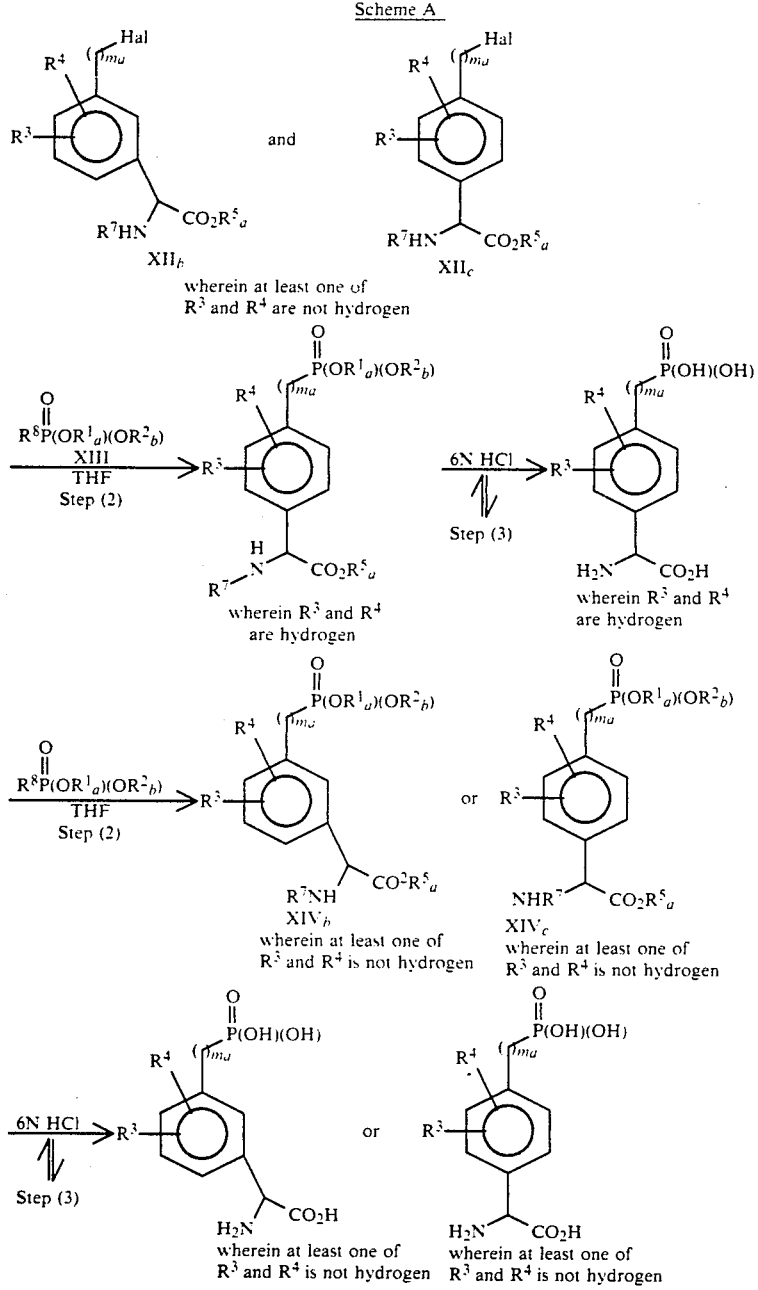

In another process of the present invention analogous to known processes the compounds of the formula I wherein groups $I_a$ and $I_b$ are meta, n is 0, and m is 1 is prepared in a process which comprises Step (1) reaction of a compound of the formula (XX)

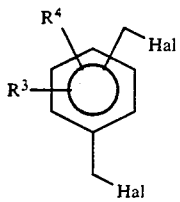

XX wherein Hal is as defined above and one Hal containing group is meta or para to the other Hal, and $R^3$ and $R^4$ are as defined above;

with a compound of the formula (XXI)

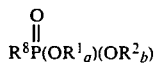

XXI wherein $R^8$, $R^1$, and $R^2$ are as defined above;

in a solvent such as diethyl ether, tetrahydrofuran, dimethylformamide, or dimethoxyethane, and the like to obtain a compound of the formula (XXII)

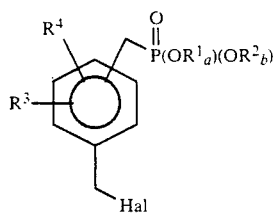

XXII wherein $R^1$, $R^2$, $R^3$, $R^4$, and Hal are all as defined above;

Step (2) Sodium in methanol, ethanol, or the like is treated with 2-nitropropane and the compound of formula XXII to obtain a compound of the formula (XXIII)

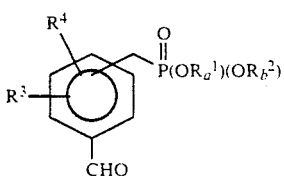

XXIII

Step (3) the compound of formula XXIII is then stirred in a solution of sodium metabisulfite in water to which concentrated ammonium hydroxide is then added followed by the addition of NaCN then protected to obtain a compound of the formula (XXIV)

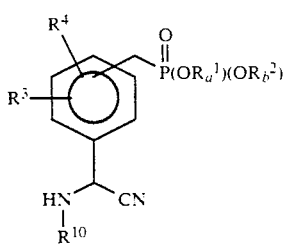

XXIV wherein $R^{10}$ is a protecting group;

Step (4) the compound of the formula XXIV is hydrolyzed to obtain the compound of formula I wherein $R^3$ and $R^4$ is as defined above and $R^1$, $R^2$, and $R^5$ is hydrogen and optionally treated further to obtain the formula I wherein $R^1$, $R^2$, and $R^5$ are an ester or amide residue or pharmacologically base salt thereof.

This process is summarized in Scheme B as follows:

Scheme B

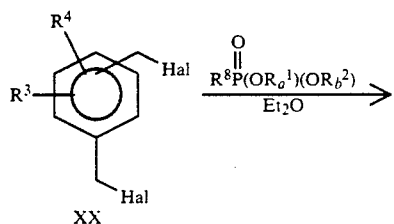

XX

-continued
Scheme B

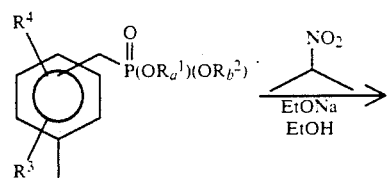

XXII

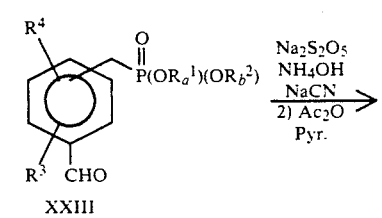

XXIII

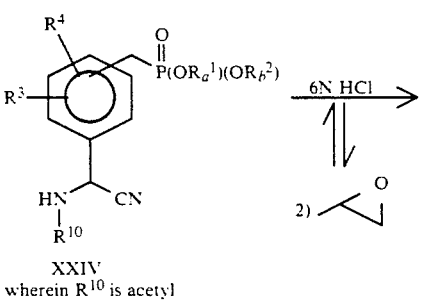

XXIV
wherein $R^{10}$ is acetyl

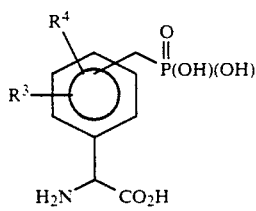

Another process to prepare the compounds of the present invention of formula I wherein one Hal containing group is meta or para to the other Hal and n is 1 and m is 1 is analogous to that of U.S. Pat. No. 4,657,899 and is shown as follows in Scheme C. Optionally, as for products shown for any scheme herein the products of this scheme can also be further reacted to obtain salts or labile esters or amides thereof.

Scheme C

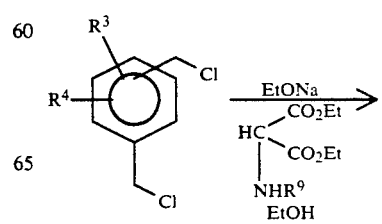

-continued

Scheme C

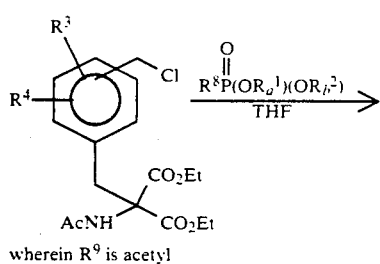
wherein R⁹ is acetyl

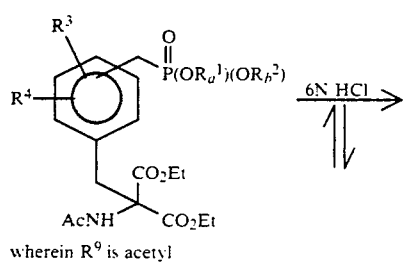
wherein R⁹ is acetyl

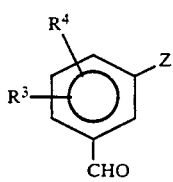

Another process of the present invention is for the preparation of compounds of the formula I wherein groups $I_a$ and $I_b$ are meta and n is 0 and m is 2 which comprises Step (1) treating a compound of the formula (XXX)

XXX wherein Z is Br or I and $R^3$ and $R^4$ are as defined above; in a solvent such as ethanol, methanol, and the like with ammonium chloride in water, then a solution of potassium cyanide also in water is added after which the product is treated with HCl in ether to obtain the compound of formula (XXXI)

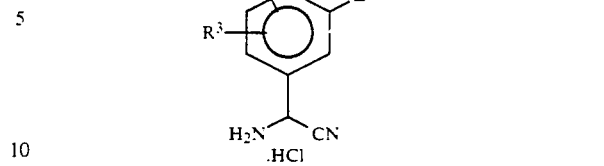
XXXI which is treated to add a protecting group to the amino substituent;

Step (2) the protected compound of formula XXXI is then treated with a compound of the formula (XXXII)

XXXII wherein $R_a^1$ and $R_b^2$ are as defined above;

in the presence of palladium acetate, tri-orthotolylphosphine and tri-n-butylamine in a solvent such as xylene, toluene, and the like to obtain the compound of the formula (XXXIII)

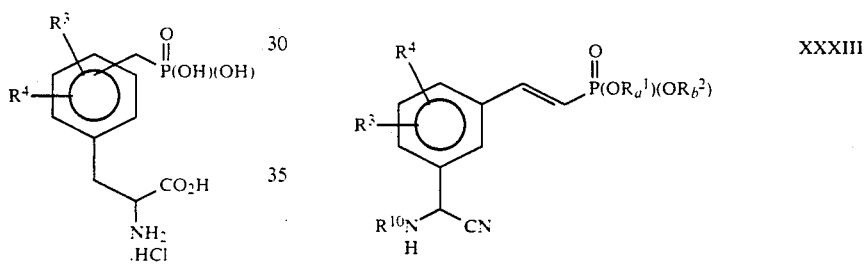
XXXIII wherein $R^{10}$ is a protecting group and $R_a^1$ and $R_b^2$ are as defined above;

Step (3) then the compound of formula XXXIII is optionally (a) hydrogenated and then hydrolyzed or (a) hydrolyzed and (b) treated to obtain the compound of formula I wherein $I_a$ and $I_b$ are meta, n is 0, m is 2, and $R^1$, $R^2$, $R^3$, $R^4$, and $R^5$ are as defined above.

This process may also be useful beginning with compounds analogous to those of the formula XXX but where the Z substituent is para to the CHO group and obtaining compounds analogous to those of the formula XXXI and XXXIII having the Z and

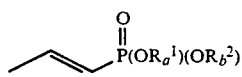

substituents in the corresponding para position to obtain the compound of formula I wherein $I_a$ and $I_b$ are para, n is 0, m is 2, and $R^1$, $R^2$, $R^3$, $R^4$, and $R^5$ are as defined above. (That is, the same process described immediately above and shown in Scheme D may be applied to corresponding compounds having para substituents.)

This process, having the substituents in the meta positions shown above, is summarized in Scheme D as follows:

Scheme D

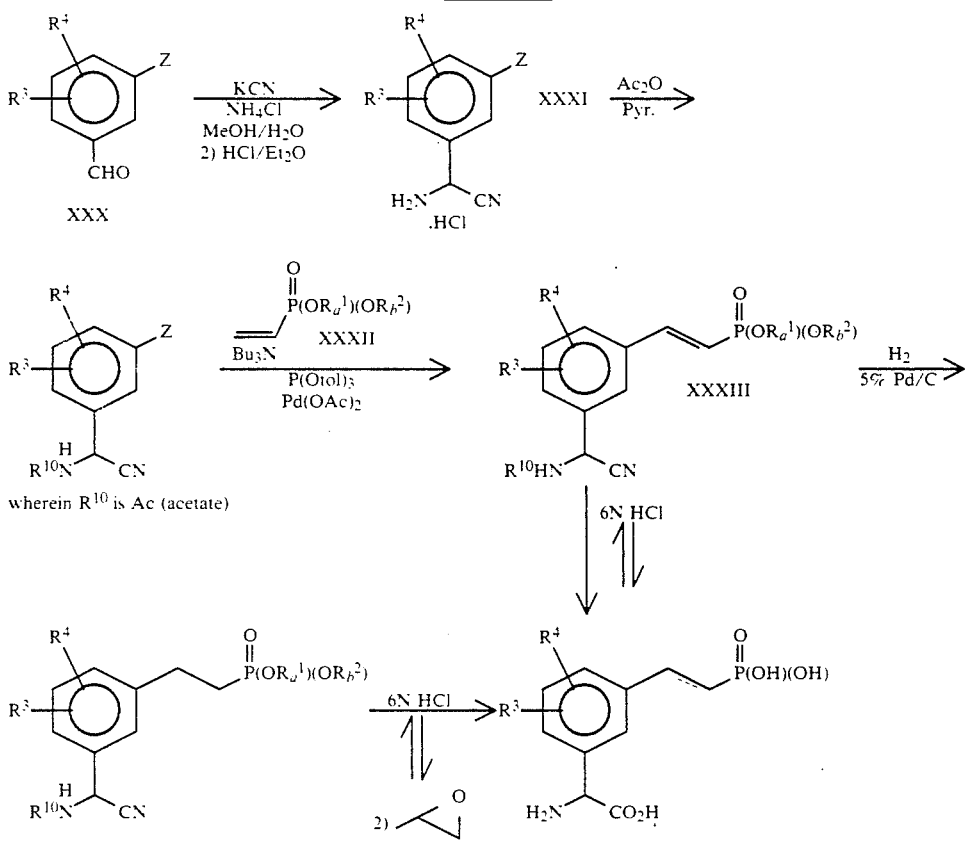

Another process of the present invention to prepare the compounds of the present invention of the formula I wherein groups $I_a$ and $I_b$ are meta and wherein n is 1 and m is 2 comprises Step (1) treating a compound of the formula XL

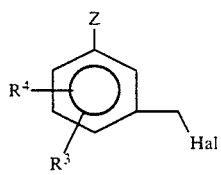
XL wherein Z is Br or I, Hal, $R^3$, and $R^4$ are as defined above with diethylacetamidomalonate, dimethylacetamidomalonate, diethylformamidomalonate, or the like in the presence of sodium in a solvent such as ethanol or methanol and the like; to obtain a compound of the formula XLI.

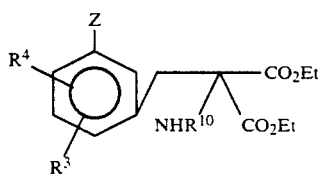
XLI wherein $R^{10}$ is as defined above and Et is ethyl;

Step (2) the compound of formula XLI is treated in a manner analogous to Steps (2) and (3) in Scheme D above to obtain the compound of formula I having $I_a$ and $I_b$ in meta positions wherein n is 1 and m is 2;

Or (Step 2) the product of Step (1) is treated with

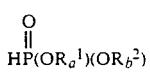

in a palladium catalyzed exchange of the Z substituent using conditions analogous to those found in *Synthesis*, 56–57, 1981 followed by hydrolysis with optional treatment to obtain a compound of the formula (XLII)

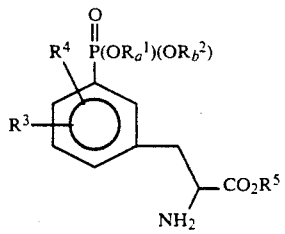
XLII which are the compounds of formula I wherein m is 0 and n is 1 and in the compounds shown $I_a$ is meta to $I_b$. For the compound of formula I wherein m is 0 and n is 1 but $I_a$ is para to $I_b$ an appropriate starting material having the Z containing substituent para to the Hal containing substituent is treated in an analogous manner to obtain the corresponding para intermediates resulting in the para product.

The substituent Z may also be selected from those known to one of ordinary skill in the art including, for example. triflates. mercuric halides. and the like. (See Heck, Richard F., "Palladium Reagents in Organic Synthesis," Academic Press (1985)).

These various process steps can be shown as follows in Scheme E for the product having $I_a$ and $I_b$ as defined above in a meta relationship, but a scheme showing the para relationship may be substituted to show the product having $I_a$ and $I_b$ in a para relationship.

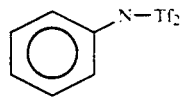

wherein Tf is

Scheme E

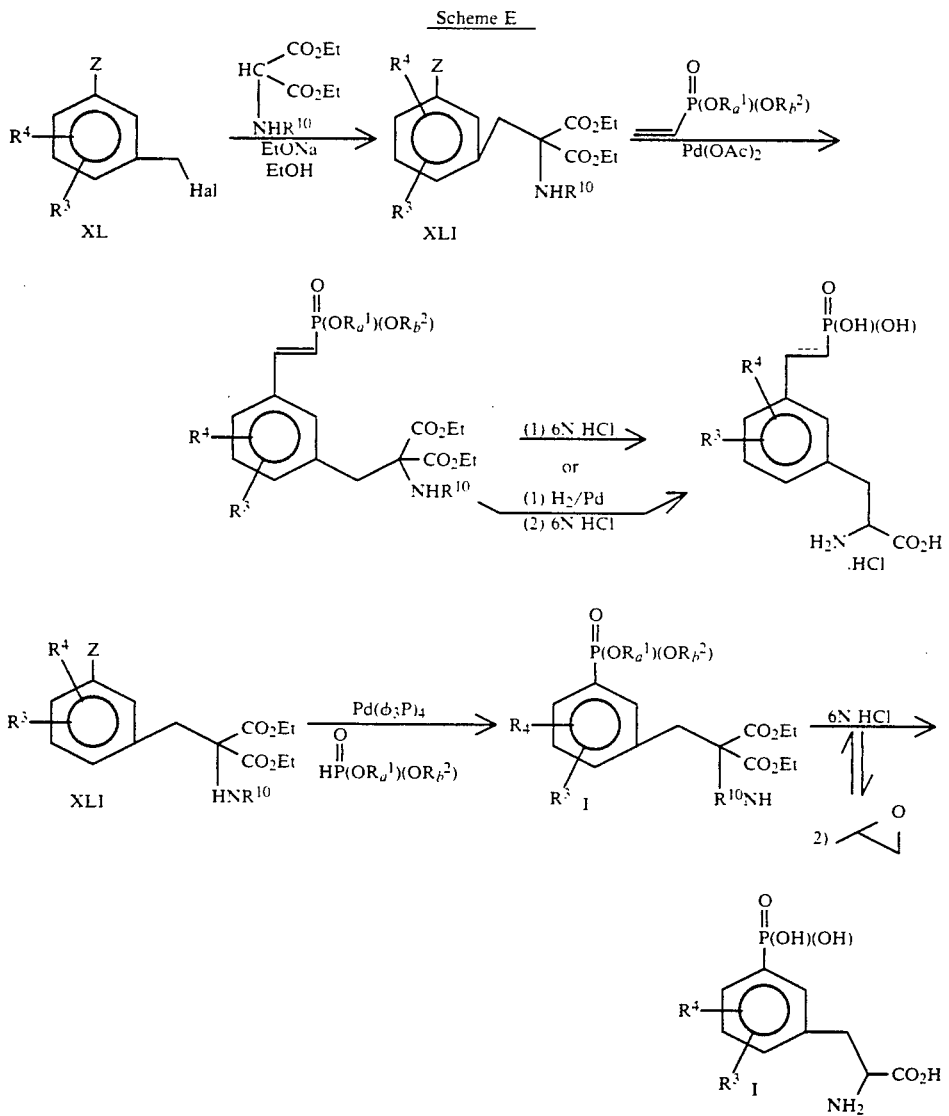

Finally, the present invention is a process for the preparation of a compound of the formula I wherein group $I_a$ and $I_b$ are meta and n is 2 and m is 0, comprising Step (1) treating a compound of the formula (LX)

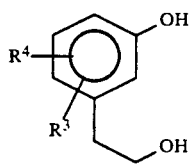

LX with bistrifluoromethanesulfonyl aniline of the formula

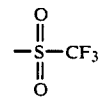

in methanol in the presence of diisopropylethylamine using conditions analogous to those described in *J. Am. Chem. Soc.*, 109(9), 2381 (1987) to obtain a compound of the formula (LXI)

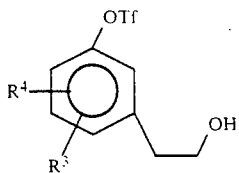

LXI wherein Tf is the triflate residue;

Step (2) the compound of the formula LXI is then treated with a compound of the formula

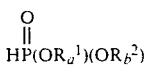

in the presence of a palladium catalyst as described in *J. Am. Chem. Soc.*, 109(9), 2381 (1987) to obtain a compound of the formula (LXII)

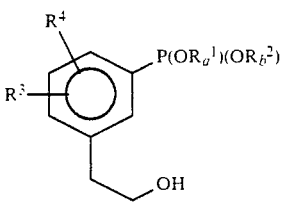

LXII

The compound of formula LXII can be treated in a manner known, or analogous to known processes, to obtain compounds of formula I wherein n is 2 and m is 0, having the $I_a$ and $I_b$ substituent in a meta relationship. Again for the compounds of formula I wherein n is 2 and m is 0 having $I_a$ and $I_b$ in a para relationship corresponding starting materials and intermediates may be used in an analogous process to this process now shown as Scheme F below.

Scheme F

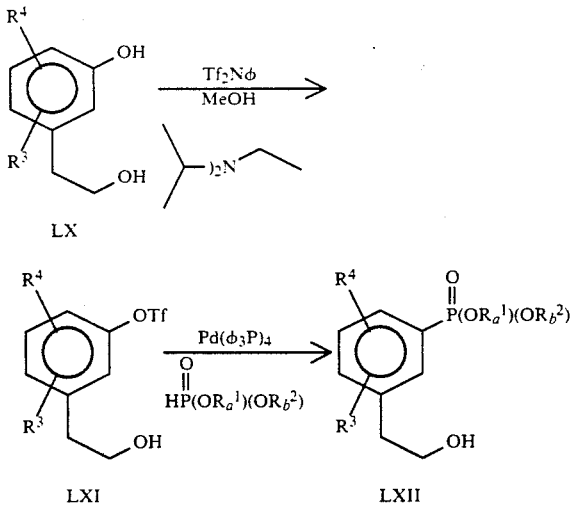

DETAILED DESCRIPTION OF THE INVENTION

In the compounds of formula I the term "lower alkyl" is meant to include a straight or branched alkyl group having one to four carbon atoms, such as, for example, methyl, ethyl, propyl, or butyl, and isomers thereof.

Pharmaceutically acceptable labile ester residues within the context of the present invention represents an ester residue of the esterified carboxy group $I_a$ or "esterified phosphono group $I_b$ above, preferably a carboxylic acid or phosphono acid prodrug ester that may be convertible under physiological conditions to free carboxy or phosphono acid groups.

That is, the pharmaceutically acceptable esterified carboxy of the group $I_a$ preferably represent e.g. lower alkoxycarbonyl; (amino, mono-, or di-lower alkylamino)-substituted straight chain lower alkoxycarbonyl, carboxy substituted lower alkoxycarbonyl, e.g. α-carboxy-substituted lower alkoxycarbonyl; lower alkoxycarbonyl-substituted lower alkoxycarbonyl, e.g. α-lower alkoxycarbonyl-substituted lower alkoxycarbonyl; aryl-substituted lower alkoxycarbonyl, e.g. unsubstituted or substituted benzyloxycarbonyl or pyridylmethoxycarbonyl; lower alkanoyloxy-substituted methoxycarbonyl, e.g. pivaloyloxymethoxycarbonyl; (lower alkanoyloxy or lower alkoxy)-substituted lower alkoxymethoxycarbonyl; bicyclo[2.2.1]heptyloxycarbonyl -substituted methoxycarbonyl, e.g. bornyloxycarbonylmethoxy-carbonyl; 3-phthalidoxycarbonyl; (lower alkyl, lower alkoxy, halo)-substituted 3-phthalidoxycarbonyl; lower alkoxycarbonyloxy-lower alkoxycarbonyl; e.g. 1-(methoxy- or ethoxycarbonyloxy)-ethoxycarbonyl.

Most preferred prodrug esters are e.g. the straight chain $C_{1-4}$-alkyl esters, e.g. ethyl; the lower alkanoyloxymethyl esters, e.g. pivaloyloxymethyl; the di-lower alkylamino-straight chain $C_{2-4}$-alkyl esters, e.g. 2-diethyl-yl-aminoethyl; the pyridylmethyl esters, e.g. 3-pyridylmethyl.

Similarly, the pharmaceutically acceptable "esterified" phosphono of the group $I_b$ preferably include equivalent representative substituents.

The labile amide residues of either the carboxy or phosphono substituent may include those amides known by artisans to be useful as prodrugs.

Lower alkoxy is -O-alkyl or of from one to four carbon atoms as defined above for "lower alkyl".

Lower alkylthio is -S-alkyl of from one to four carbons.

Appropriate compounds of formula I are useful in the free base form, in the form of base salts where possible, and in the form of acid addition salts. The three forms are within the scope of the invention. In practice, use of salt form amounts to use of the base form. Pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfonate, ethanesulfonate, benzenesulfonate, p-toluenesulfonate, and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1):1-19 (1977).)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The compounds of the invention contain one or more asymmetric carbon atoms. Thus, the invention includes the individual stereoisomers, and mixtures thereof. The individual isomers may be prepared or isolated by methods known in the art.

One of skill in the art would recognize variations in the sequence and would recognize appropriate reaction conditions from analogous reactions which may be appropriately used in the processes to make the compounds of formula I herein. Further, the starting materials are known or can be prepared by known methods.

Under certain circumstances it is necessary to protect the N of intermediates in the above noted process with suitable protecting groups which are known. Introduction and removal of such suitable nitrogen protecting groups are well-known in the art of organic chemistry; see for example, "Protective Groups in Organic Chemistry," J. F. W. McOmie, ed., (New York, 1973), pages 43ff, 95ff, J. F. W. McOmie, *Advances in Organic Chemistry*, Vol. 3, 191-281 (1963); R. A. Borssona, *Advances in Organic Chemistry*, Vol. 3, 159-190 (1963); and J. F. W. McOmie, *Chem. & Ind.*, 603 (1979).

In the process described herein for the preparation of compounds of this invention the requirements for protective groups are generally well recognized by one skilled in the art of organic chemistry, and accordingly the use of appropriate protecting groups is necessarily implied by the processes of the charts herein, for example, the protecting groups must be stable to the conditions of the processes, although not expressly illustrated.

Starting materials for the processes described above are known or can be prepared by known processes.

The products of the reactions described herein are isolated by conventional means such as extraction, distillation, chromatography, and the like.

The salts of the compounds of formula I described above are prepared by reacting the appropriate base or acid with a stoichiometric equivalent of the compounds of formula I, respectively, to obtain pharmaceutically acceptable salts thereof.

The preferred compounds of the present invention are of the formula I wherein when the groups $I_a$ and $I_b$ are in the meta position then n is 1 and m is 1 or 2 and also then n is 2 and m is 0; or when the groups $I_a$ and $I_b$ are in the para position then n is 0 and m is 1.

The most preferred compounds of the present invention are benzeneacetic acid, α-amino-3-(phosphonomethyl); benzeneacetic acid, (±)-α-amino-4-(phosphonomethyl); and phenylalanine, 3-phosphonomethyl. Of these most preferred the most active compound is benzeneacetic acid, (±)-α-amino-4-(phosphonomethyl).

The activity of the compounds of the formula I is shown in vitro in an NMDA receptor binding assay based on the use of [$^3$H]CPP as antagonist ligand in a manner essentially as set out by B. E. Murphy et al in *J. Pharm. Exp. Ther.*, 240, 778 (1987). The following activity is noted in Table 1 below.

TABLE 1

| Example | Activity (CPP Binding) | |
|---|---|---|
| | $IC_{50}$ ($10^{-6}$ M) | % at $10^{-4}$ M |
| APH | 0.80 | |
| I | | 20 |
| II | 11.8 | |
| III | 3.56 | |
| IV | | 35 |
| V | | 15 |
| VI | | 10 |
| VII | | 19 |
| VIII | 0.99 | |
| IX | | 4 |
| X | | 10 |
| VI A | 17.9 | 90 |

The compounds of the present invention are antagonists as shown by the profile of selected compounds. That is, the compounds are inhibitors of [$^3$H]TCP tissue binding in an in vitro assay described in *Eur. J. Pharmacol.*, 123, 467 (1986) and *Neurosci. Lett.*, 76, 221 (1987) and inhibition of glutamate stimulated acetylcholine release from striatal slice preparations as disclosed in *J. Pharm. Exp. Ther.*, 240, 737 (1987).

In vivo activity for the compounds of the present invention is shown by selected compounds in the following assays which are generally accepted to establish the utility for the treatment of diseases as noted above.

Inhibitory Effects in NMDA-Induced

Subconvulsant Behavior in Fisher Rats

In mice, the induction of tonic/clonic seizures (Czuczwar, S. J. and B. Meldrum, "Protection against chemically induced seizures by 2-amino-7-phosphonoheptanoic acid," *Eur. J. of Pharm.*, 83 335-339 (1982) and Czuczwar, S. J. et al, "Antagonism of N-methyl-D,L-aspartic acid-induced convulsions by antiepileptic drugs and other agents," *Eur. J. of Pharm.*, 108, 273-280 (1985)) and subconvulsant compulsive tail biting/hind limb scratching (Models of N-methyl-D-aspartate antagonism: A comparison of 2-amino-7-phosphonoheptanoic acid with muscle relaxant drugs, 15th Annual Meeting, International Society for Neuroscience (1985)) by intraperitoneal or subcutaneous injection of the excitatory amino acid N-methyl-D-aspartic acid (NMDA) ($\geq 100$ mg/kg) has been previously reported. In a modification of those methods, subconvulsant tail biting was induced in Fisher rats by intravenous injection of 50 mg/kg NMDA. The incidence (%) and response time (60 minutes=maximum) of control and drug treated rats (I.P., 30 minutes before NMDA) were compared. The inhibitory effects of 2-amino-7-phosphonoheptanoic acid and Example VIII are shown in Table 2 (% responders and time (latency in minutes)).

TABLE 2

| Treatment* | % Responders | % I** | Latency (min ± *S.E.) |
|---|---|---|---|
| Saline | 9/11 | | 33.1 ± 5.8 |
| 7-APH 30 mg/kg | 1/10 | 87.8 | 59.0 ± 1.0≈ |
| Saline | 9/10 | | 15.8 ± 5.3 |

TABLE 2-continued

| Treatment* | % Responders | % I** | Latency (min ± *S.E.) |
|---|---|---|---|
| 7-APH 10 mg/kg | 6/10 | 33.3 | 43.3 ± 5.8≈≈ |
| Phosphate buffer | 9/10 | | 24.8 ± 4.9 |
| Example VIII 37 mg/kg | 1/10 | 88.9 | 55.5 ± 4.5≈≈ |
| Example VIII 25 mg/kg | 2/9 | 77.8 | 51.6 ± 5.6≈ |

*Rats were dosed IP, 2 mls/kg 30 min before NMDA.
**% I = [1 − % test responders/% control responders] · 100.
≈p < 0.01.
≈≈p < 0.001.

As shown in Table 2, Example VIII showed inhibitory effects similar in potency and efficacy to 7-APH. At zero to thirty minutes before rats were dosed with NMDA and sixty minutes after, rats were observed for drug effects or normal behavior. Rats dosed with 30 mg/kg 7-APH showed no ataxia, but were slightly less exploratory than controls. Rats dosed with 10 mg/kg 7-APH, or Example VIII (37 mg/kg and 25 mg/kg) showed no drug induced behavioral effects.

Additional In Vivo Data Showing

NMDA Inhibition

Intraperitoneal injection of N-methyl-D-aspartic acid (NMDA) has been previously reported to induce clonic seizures in C57BL/6J mice (Bernard, P.S. et al, Models of N-methyl-D-aspartate antagonism: A comparison of 2-amino-7-phosphonoheptanoic acid with muscle relaxant drugs, 15th Annual Meeting, International Society for Neuroscience, 1985). In a modified version of the above protocol, male CF-1 mice received an intravenous injection of 25 mg/kg NMDA—behind the lateral aspect of the right eye. This induced a rapidly onsetting seizure followed shortly thereafter by death. Drug treatments were administered intravenously behind the left eye five minutes prior to NMDA administration. Immediately following NMDA injection animals were observed for seizure activity and survivors were quantitated thirty minutes post injection. $ED_{50}$ were determined for inhibition of seizures and death through comparison of drug treatment groups (n=10) with their respective vehicle controls (n=10). The data is shown in Table 3.

TABLE 3

| Compound PD Number | Inhibition of Seizures $ED_{50}$ mg/kg | Inhibition of Death $ED_{50}$ mg/kg |
|---|---|---|
| APH | >30 | 30 |
| Example VIII | >30 | 7.6 |
| Example III | ≈60 | 37 |

Therefore, the compounds of formula I and their pharmacologically acceptable acid addition salts are effective agents in the prophylaxis and/or therapeutic treatment of disorders responsive to agents which block NMDA receptors, thus forming a further aspect of the present invention in like manner.

For medical use, the amount required of a compound of formula I or pharmacologically acceptable salt thereof— (hereinafter referred to as the active ingredient) to achieve a therapeutic effect will, of course, vary both with the particular compound, the route of administration and the mammal under treatment and the particular disorder or disease concerned. A suitable systemic dose of a compound of formula I or pharmacologically acceptable salt thereof for a mammal suffering from, or likely to suffer from any condition as described hereinbefore is in the range 0.01 to 100 mg of base per kilogram body weight, the most preferred dosage being 0.05 to 50 mg/kg of mammal body weight.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by intravenous infusion and repeated administrations, parenterally or orally, as considered appropriate.

While it is possible for an active ingredient to be administered alone, it is preferable to present it as a formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

Formulations suitable for parenteral administration conveniently comprise a sterile aqueous preparation of the active ingredient which is preferably isotonic with the blood of the recipient.

Formulations suitable for nasal or buccal administration, (such as self-propelling powder dispensing formulations described hereinafter), may comprise 0.1 to 20% w/w, for example 2% w/w of active ingredient.

The formulations, for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

So the pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose, and/or glycine; b) lubricants, e.g. silica, talcum, stearic acid, its magnesium or calcium salt, and/or polyethyleneglycol; for tablets also; c) binders e.g. magnesium aluminum silicate, starch paste, gelatin, tragacanth, methylcellulose, sodium carboxymethylcellulose and/or polyvinylpyrrolidone; if desired d) disintegrants, e.g. starches, agar, alginic acid, or its sodium salt, or effervescent mixtures; and/or e) absorbents, colorants, flavors, and sweeteners. Injectable compositions are preferably aqueous isotonic solutions or suspensions, and suppositories are advantageously prepared from fatty emulsions, or suspensions. Said compositions may be sterilized and/or contain adjuvants, such as preserving, stabilizing, wetting or emulsifying agents, solution promoters, salts for regulating the osmotic pressure, and/or buffers. In addition, they may also contain other therapeutically valuable substances. Said compositions are prepared according to conventional mixing, granulating, or coating methods, respectively, and contain about 0.1 to 75%, preferably about 1 to 50%, of the active ingredient.

The formulations may conveniently be presented in unit dosage form and may be prepared by any of the methods well-known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Finally, the present invention is a method of prophylactic or therapeutic treatment of cerebral ischemia, cerebral infarction, thromboembolic or hemorrhagic stroke, cerebral vasospasm, hypoglycemia, cardiac arrest, status epilepticus, schizophrenia, epilepsy, neurodegenerative disorders, Alzheimer's disease, Huntington's disease, or risk of cerebrovascular damage which comprises administering an antagonist effective amount for excitatory amino acid receptors of a compound of the formula I in unit dosage form.

The invention is further elaborated by the representative examples as follows. Such examples are not meant to be limiting.

EXAMPLES

Preparation I

α-(Benzolyamino)-4-(3-Bromopropyl)Benzenacetic Acid

Bromopropyl benzene (78 g, 0.4 mol, Aldrich) is combined with methanesulfonic acid (100 ml) and the reagents vigorously stirred as α-hydroxyhippuric acid (19.5 g, 0.1 mol, Aldrich) is added in one portion. Stirring is maintained forty-eight hours and the reaction poured into 1 liter of water which is extracted 2×500 ml ethyl acetate. The organic extracts are combined, extracted with 1N NaOH (3×250 ml), washed with toluene (250 ml), and acidified to pH 2 with 3N HCl. The separated material is taken up by extraction with ethyl acetate (2×250 ml) which is dried (MgSO$_4$), concentrated, and the solid recrystallized from ethyl acetate/toluene (250 ml, 20%). A solid was obtained (16.1 g, 43%), mp 135-6.

Preparation II

α-(Benzoylamino)-4-[3-Diethoxyphospinyl)Propyl] Benzenacetic Acid Hydrochloride

A sodium hydride dispersion (3.3 g of a 60% dispersion, 85 mmol) is washed with heptane (25 ml) under nitrogen, suspended in dry THF (80 ml), and stirred at room temperature. A solution of diethyl phosphite (14.7 g, 110 mmol, Aldrich) in dry THF (20 ml) is added dropwise over thirty minutes as gas is evolved. A solution of α-(benzoylamino)-4-[3-bromopropyl]benzeneacetic acid (8.0 g, 21.3 mmol) in dry THF (25 ml) is then added dropwise and the reaction stirred at room temperature overnight. The reaction is concentrated, taken up in a mixture of 250 ml ethyl acetate and 50 ml 1N HCl and the ethyl acetate washed with 50 ml fresh 1N HCl. The organics are extracted with 1N NaOH (4×50 ml) and the product obtained by acidification of the stirred NaOH extracts with concentrated HCl. A solid forms which is filtered, washed with water, and air dried. The material is purified by precipitation from a methanolic solution with diethyl ether. A fine white solid was obtained (7.1 g, 77%) with mp 167-8.

EXAMPLE I

Benzeneacetic Acid, α-Amino-4-(3-Phosphonopropyl) -Hydrochloride, (±)-

α-(Benzoylamino)-4-[3-(diethoxyphosphin-vl)propyl]benzene-acetic acid (6.0 g, 13.8 mmol) is suspended in 6N HCl (300 ml) and heated to reflux. The solid is taken up after two hours and the solution refluxed twenty-four hours. The reaction is refrigerated overnight, the precipitated benzoic acid is filtered and the filtrate is concentrated to a viscous residue, reconcentrated twice from water and dried in vacuo at room temperature. The solid obtained is triturated with acetone and dried at 78° C. in vacuo to give 3.9 g (91%) of the hydrochloride salt of α-amino-4-(3-phosphonopropyl) benzeneacetic acid. Melting point: foams on heating over 210° C.

Preparation III

[[3-(Bromomethyl)Phenyl]Methyl]Phosphonic Acid, Diethyl Ester m-Dibromoxylene (28.1 g, 0.106 mol, Aldrich) is dissolved in diethyl ether (400 ml) and cooled in an ice/salt bath under nitrogen. A suspension of sodium diethylphosphite in diethyl ether is then prepared as follows: a 60% NaH dispersion (4.3 g, 0.106 mol) is washed twice with 25 ml heptane under nitrogen, suspended in diethyl ether (100 ml) and stirred while a solution of diethyl phosphite (20.7 g, 0.15 mol) is added dropwise at a rate to maintain a controlled gas evolution. After the addition is complete, the reaction is stirred thirty minutes and transferred to an addition funnel and added dropwise over twenty minutes to the cold solution of the dibromide. After one hour the bath is removed and the reaction stirred at room temperature overnight. The solids are filtered and the residue taken up in toluene and chromatographed on 150 g silica to give a colorless oil (7.1 g, 21%).

Preparation IV

[3-Formylphenyl)Methyl]Phosphonic Acid Diethyl Ester

Sodium (0.39 g, 16.8 mmol) is added in pieces to absolute ethanol (17 ml) and stirred until the solid is taken up. 2-Nitropropanol 1.91 g, (21.4 mmol) is added and the reaction deposits a solid. After thirty minutes a solution of bromide [[3-bromomethyl)phenyl]methyl]phosphonic acid, diethyl ester (4.9 g, 15.3 mmol) in ethanol (15 ml) is added dropwise to give a homogeneous reaction. The reaction is stirred at room temperature overnight, the solids filtered, and the reaction concentrated. The residue is taken up in a mixture of 150 ml ethyl acetate and 25 ml water, the layers separated, and the organic phase washed twice with 1N NaOH (25 ml). The ethyl acetate is dried (MgSO$_4$), concentrated, and the oil chromatographed on silica to afford the aldehyde (3.0 g, 77%).

Preparation V

[[3-[(Acetylamino)Cyanomethyl]Phenyl]Methyl]Phosphonic Acid,

Diethyl Ester

[(3-Formylphenyl)methyl]phosphonic acid diethyl ester (0.78 g, 3.0 mmol) is added to a stirred solution of sodium metabisulfite (0.29 g, 1.5 mmol) in 3 ml water. Concentrated ammonium hydroxide (0.6 ml) is added and the reaction stirred ten minutes before sodium cyanide (0.15 g, 3.0 mmol) is added in one portion. After three hours the reaction is extracted 3×5 ml ethyl acetate and the organics extracted 2×6 ml 1N HCl. The acid is combined with 10 ml ethyl acetate and neutralized by slowly adding sodium carbonate. The layers are separated and the water washed with 10 ml ethyl acetate.

The organics are dried (MgSO$_4$) and concentrated to an oil (0.44 g) which is dissolved in pyridine (3 ml), cooled in an ice bath and treated with acetic anhydride (0.31 g, 3.0 mmol). The reaction is stirred overnight and the solvents concentrated. The residue is taken up in ethyl acetate (5 ml) and washed with 1N HCl (1 ml), saturated bicarbonate (1 ml), and dried (MgSO$_4$). The solvent is concentrated and the product purified by chromatography on silica to give [[3-[(acetylamino)cyanomethyl]phenyl]methyl]phosphonic acid, diethyl ester as a colorless oil (0.25 g).

EXAMPLE II

Benzeneacetic Acid, α-Amino-3-(Phosphonomethyl)-

The precursor [[3-[(acetylamino)cyanomethyl]phenyl]methyl]phosphonic acid, diethyl ester is hydrolyzed as described in Example I above. The free base is prepared by dissolving the hydrochloride salt in methanol and treating with propylene oxide. The product precipitates as a light brown solid, mp foams over 180° C.

Preparation VI (Acetylamino)[3-(Chloromethyl)Phenyl]Methyl]-Propanedioic

Acid, Diethyl Ester

Sodium (1.15 g, 50 mmol) is added to absolute ethanol (100 ml) and the reaction stirred until the sodium is taken up. Diethylacetamidomalonate (10.9 g, 50 mmol, Aldrich) is added in one portion and the reaction stirred thirty minutes before a solution of m-dichloroxylene (8.75 g, 50 mmol, Aldrich) in dry THF (40 ml) is added dropwise. The reaction is stirred at room temperature overnight and the ethanol is concentrated. The unreacted dichloride is removed by precipitation of the reaction solids from ether with heptane. The solvents are concentrated to give a solid which was dried. The product is dissolved in a small volume of ether which is heated on a steam bath, the di-adduct filtered, and heptane is added. The product crystallized and is filtered and dried to give 7.1 g (40%) of (acetylamino)[[3-(chloromethyl)phenyl]methyl]propanedioic acid, diethyl ester.

Preparation VII (Acetylamino)[[3-[(Diethoxyphosphinyl)Methyl]Phenyl]]

Methyl]Propanedioic Acid, Diethyl Ester

A sodium dispersion (60% in oil, 0.98 g, 24.4 mmol) is washed with heptane, suspended in dry THF (15 ml), and stirred as a solution of diethyl phosphite (3.9 g, 28.2 mmol) in dry THF (15 ml) is added slowly to give a solution. After thirty minutes a solution of the benzylic chloride (acetylamino)[[3- (chloromethyl)phenyl]methyl]propanedioic acid, diethyl ester in dry THF (15 ml) is added dropwise over fifteen minutes and the reaction stirred at room temperature overnight. The solvent is concentrated and the residue taken up in ethyl acetate, washed twice with water, dried over Na$_2$SO$_4$, and concentrated to an oil which is crystallized by heating in heptane on a steam bath and adding ethyl acetate until the oil dissolved. A crystalline solid (5.2 g, 61%) precipitated upon cooling which is isolated by filtration.

EXAMPLE III

Phenylalanine, 3-(Phosphonomethyl)

The tetraester precursor (acetylamino)[[3-[diethoxyphosphinyl)methyl]phenyl]methyl]propanedioic acid, diethyl ester (5.1 g) is hydrolyzed by refluxing for twenty-four hours in 200 ml 6N HCl. The solvent is concentrated to a thick residue which was taken up in ethanol (125 ml) and treated with propylene oxide (1.0 g). A precipitate slowly forms which is filtered, washed with ethanol and ether, and dried to afford a white solid (1.9 g, 66%). Melting point: foams at 215° C. then slowly decomposes.

Preparation VIII

α-Amino-3-Bromobenzeneacetonitrile, Monohydrochloride

A solution of 3-bromobenzaldehyde (18.5 g, 0.1 mol) is dissolved in methanol (15 ml) and stirred at room temperature as a solution of ammonium chloride (5.35 g, 0.1 mol) in water (12.5 ml) is added in one portion. After thirty minutes a solution of potassium cyanide (6.5 g, 0.1 mol) in water (12.5 ml) is added in one portion and the reaction stirred overnight. The mixture is then refluxed one hour, allowed to cool, and the separated oil extracted into diethyl ether and treated with an ethereal solution of hydrogen chloride to give a brown solid. This is recrystallized by dissolving in methanol (100 ml), diluting with diethyl ether (450 ml), and refrigerating the solution overnight. The solid obtained is filtered, washed with ether, and dried (3.5 g).

Preparation IX

N-[(3-Bromophenyl)Cyanomethyl]Acetamide

The amine salt α-amino-3-bromobenzeneacetonitrile, monohydrochloride (2.7 g, 10.9 mmol) is added to 25 ml pyridine cooled in an ice bath. The solution is stirred thirty minutes, treated with acetic anhydride (2.2 g, 1.8 mmol), and the reaction stirred two hours at room temperature. The pyridine is concentrated and water (25 ml) is added to give a solid which is filtered and recrystallized from ethyl acetate/heptane (2.3 g, 83%).

Preparation X (E)-[2-[3-[(Acetylamino)Cyanomethyl]Phenyl]Ethenyl] Phosphonic Acid, Diethyl Ester Xylene (6 ml) is degassed and stirred under nitrogen. Palladium acetate (40 mg, 0.17 mmol) and tri-orthotolylphosphine (210 mg, 0.69 mmol) are added at room temperature, followed by freshly distilled tri-n-butylamine (2.0 g, 10.9 mmol), freshly distilled diethyl vinylphosphonate (1.8 g, 10.9 mmol), and the aryl bromide N-[(3-bromophenyl) cyanomethyl]acetamide (2.2 g, 8.7 mmol). The reaction is heated to 115° C. in an oil bath and maintained for one and one-half hours, allowed to cool to room temperature, and diluted with ethyl acetate. The organics are washed with water, 1N HCl, and saturated bicarbonate solution then dried (MgSO$_4$) and concentrated. Chromatography afforded a purified oil (2.4 g, 89%).

Preparation XI

[2-[3-[(Acetylamino)Cyanomethyl]Phenyl] Ethyl]Phosphonic Acid, Diethyl Ester

Reduction of (E)-[2-[3-[(acetylamino)cyanomethyl]-phenyl]ethenyl]phosphonic acid, diethyl ester prepared in Preparation X above (2.30 g, 6.8 mmol) is accomplished in ethanol using 5% Pd/C @50 psi. The reaction is monitored by nmr, following the disappearance of the vinyl protons. Upon completion the palladium catalyst is filtered, the ethanol concentrated, and the oil chromatographed on silica to give a viscous oil (1.3 g, 56%).

EXAMPLE IV

Benzeneacetic Acid, α-Amino-4-(2-Phosphonoethyl)-, (±)-

The hydrolysis of [2-[3-[(acetylamino)cyanomethyl]-phenyl]ethyl]phosphonic acid, diethyl ester is carried out in refluxing 6N HCl for twenty hours. The reaction is concentrated, reconcentrated from water then three times from acetone, and dried at 78° C. in vacuo. The free base is obtained by dissolving the residue in 25 ml methanol and treating with a slight excess of propylene oxide (0.28 g in 1 ml methanol). The free base (0.59 g) is filtered, washed with methanol, and dried at 78° C. in vacuo (mp >290° C.).

Preparation XIII

Two compounds (para and meta) within the general formula XLI above are prepared. Sodium (0.46 g, 20 mmol) is added in pieces to absolute ethanol (40 ml). After the solid was taken up, diethylacetamidomalonate (4.8 g, 22 mmol) was added in one portion, the reaction stirred fifteen minutes, and a solution of p-bromobenzyl bromide (5.0 g, 20 mmol) in dry THF (15 ml) was added. The reaction was stirred overnight at room temperature, diluted with ether, and filtered. The filtrate was concentrated to a solid which was recrystallized from 10% ethyl acetate/heptane to give the product (4.8 g, 63%); mp 132°–132.5° C.

Preparation XIV

The two corresponding aryl phosphonates of the formula XLII shown in Scheme E were prepared by a palladium catalyzed exchange for the two aryl bromides of Preparation XIII above. A general literature procedure of Synthesis, 56–57 (1981) was utilized for this exchange.

The corresponding aryl phosphonates from Preparation XIV are hydrolyzed and the free bases are obtained in a manner analogous to that described in Example IV above to give the following compounds of Examples V, VI and VI A.

EXAMPLE V

Dl-Phenylalanine, 3-Phosphono (Meta) mp: foams above 195, darkens over 250° C.

EXAMPLE VI

Dl-Phenylalanine, 4-Phosphono (Para) mp: slow decomposition over 235° C.

EXAMPLE VI A (±)-α-Amino-3-Phosphonobenzeneacetic Acid mp: >305° C.

EXAMPLE VII

Dl-Phenylalanine, 3-(2-Phosphonoethyl)-, Monohydrochloride

This analog is prepared from the compound of Preparation XIII above utilizing the methodology analogous to that of Preparations VIII, IX, X, and XI and Example IV above using appropriate starting materials. The product was isolated as the hydrochloride salt, mp foams @90°–100° C.

EXAMPLE VIII (±)-α-Amino-4-(Phosphonomethyl)Benzeneacetic Acid

This compound is prepared in a manner corresponding to the procedure for the Preparations I and II and Example I above.

EXAMPLE IX (±)-α-Amino-4-(2-Phosphonoethyl)Benzeneacetic Acid

This compound is prepared in a manner corresponding to the procedure for the Preparations I and II and Example I above.

EXAMPLE X

α-Amino-4-Phosphonobenzeneacetic Acid, Monohydrochloride

This compound is prepared in a manner corresponding to the procedure for the Preparations I and II and Example I above; mp>295° C.

We claim:

1. A compound of the formula

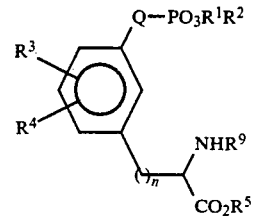

or a pharmaceutically acceptable acid addition, or base salt thereof wherein (1) n is 0, 1, or 2;

(2) $R^1$, $R^2$ and $R^5$ are independently hydrogen or a pharmaceutically acceptable labile ester or amide residue;

(3) $R^3$ and $R^4$ are independently hydrogen, hydroxy, lower alkyl optionally substituted by hydroxy or methoxy, aryl, aralkyl, lower alkoxy, $R^{10}S(O)_{0-1}(CH_2)_q$ wherein q is 0, 1, or 2 and $R^{10}$ is lower alkyl, halogen, trifluoromethyl, or $R^3$ and $R^4$ when on adjacent ring carbons are together —CH=CH—CH=CH—;

(4) $R^9$ is a hydrogen or a protective group;

(5) Q is —$(CH_2)_m$—(CH=CH)—, —$CH_2$—(CH=CH)—, or (CH=CH)—$CH_2$—wherein m is 0, 1, 2, or 3.

2. A compound of claim 1 wherien $R^1$, $R^2$, and $R^5$ are independently hydrogen, lower alkyl, lower alkanoyloxymethyl, di-lower alkylamino-straight chain alkyl of from two to four carbons; or pyridylmethyl.

3. A compound of claim 2 wherein $R^1$, $R^2$, and $R^5$ are independently hydrogen or lower alkyl.

4. A compound of claim 3 which is a α-amino-3-(phosphonomethyl)benzeneacetic acid.

5. The hydrochloride salt of the compound of claim 4.

6. A compound of claim 3 which is 3-(phosphonomethyl) phenylalanine.

7. The hydrochloride salt of the compound of claim 6.

8. A compound of claim 3 which is 3-phosphono-DL-phenylalanine.

9. The hydrochloride salt of the compound of claim 8.

10. A compound of claim 3 which is 3-(2-phosphonoethyl)-DL-phenylalanine.

11. The monohydrochloride salt of the compound of claim 10.

12. A compound of claim 3 which is (±)-α-amino-3-phosphonobenzeneacetic acid.

13. A pharmaceutical composition for treating disorders responsive to the blockade of aspartate or glutamate receptors which comprises an amount of the compound of claim 1 effective for blocking the receptors and a pharmacologically acceptable carrier.

14. A method for treating disorders responsive to the blockade of glutamate or aspartate receptors in a human suffering therefrom which comprises administering a compound of claim 1 in unit dosage form.

* * * * *